United States Patent [19]
Serbiak et al.

[11] Patent Number: 5,248,309
[45] Date of Patent: Sep. 28, 1993

[54] THIN SANITARY NAPKIN HAVING A CENTRAL ABSORBENT ZONE AND A METHOD OF FORMING THE NAPKIN

[75] Inventors: Paul J. Serbiak, Appleton; David R. King; Patricia A. Mitchler, both of Neenah; Alice Y. Romans-Hess, Fremont; Thomas W. Van Den Bogart, Kimberly; Robert J. Peerenboom, Little Chute; Valerie V. Finch; James J. Hlaban, both of Neenah, all of Wis.

[73] Assignee: Kimberly-Clark Corporation, Neenah, Wis.

[21] Appl. No.: 859,630

[22] Filed: Mar. 20, 1992

Related U.S. Application Data

[63] Continuation of Ser. No. 556,694, Jul. 19, 1990, abandoned.

[51] Int. Cl.⁵ .............................................. H61F 13/15
[52] U.S. Cl. ................................. 604/368; 604/378; 604/385.1; 604/374; 604/387; 604/365
[58] Field of Search ............... 604/368, 367, 370, 372, 604/375, 378-383, 385.1, 386, 387, 388, 365, 366, 369, 371, 374, 376, 377, 384, 385.82, 389, 390

[56] References Cited

U.S. PATENT DOCUMENTS

| 32,649 | 4/1988 | Brandt et al. | 604/368 |
|---|---|---|---|
| 2,092,346 | 9/1937 | Arone | 128/284 |
| 2,662,527 | 12/1953 | Jacks | 128/290 |
| 3,065,751 | 11/1962 | Gobbo | 128/287 |
| 3,294,091 | 12/1966 | Morse | 128/290 |
| 3,301,746 | 1/1967 | Sanford et al. | 162/113 |
| 3,397,697 | 8/1968 | Rickard | 128/288 |
| 3,455,303 | 7/1969 | Wilson | 128/289 |
| 3,570,491 | 3/1971 | Sneider | 128/290 |

(List continued on next page.)

FOREIGN PATENT DOCUMENTS

| 0122042 | 10/1984 | European Pat. Off. . | |
|---|---|---|---|
| 0165807 | 12/1985 | European Pat. Off. . | |
| 0215417A1 | 9/1986 | European Pat. Off. . | |
| 0202127 | 11/1986 | European Pat. Off. . | |
| 0248584 | 12/1987 | European Pat. Off. . | |
| 0336578 | 10/1989 | European Pat. Off. | 13/16 |
| 0339461 | 11/1989 | European Pat. Off. | 13/18 |
| 52-20692 | 2/1977 | Japan . | |
| 52-44999 | 4/1978 | Japan . | |

(List continued on next page.)

OTHER PUBLICATIONS

"Stiffness of paper (Gurley type stiffness tester)", T 543 pm-84, vol. 1, 1989 *TAPPI Journal*, Technology Parks/Atlanta, P.O. Box 105113, Atlanta, GA 30348.

"Gurley Model 4171-D Digital Stiffness Tester", 1988 Teledyne Gurley trade brochure, Teledyne Gurley, 514 Fulton St., Troy, NY, 12181-0088.

*Primary Examiner*—Randall L. Green
*Assistant Examiner*—K. M. Reichle
*Attorney, Agent, or Firm*—Thomas J. Connelly

[57] ABSTRACT

A thin sanitary napkin is disclosed along with its method of manufacture. The napkin has a liquid-impermeable baffle and an absorbent retained on the baffle. The absorbent has a longitudinally-extending central absorbent zone with a width of less than about 2 inches. The central zone is capable of absorbing at least 20 grams of body fluid which is discharged from the vaginal cavity and deposited onto the napkin. The central zone also has a greater stiffness than adjacent portions of the napkin so as to resist twisting and bunching during use. The sanitary napkin further has a caliper of less than about 5 millimeters.

19 Claims, 6 Drawing Sheets

U.S. PATENT DOCUMENTS

| | | | |
|---|---|---|---|
| 3,670,731 | 6/1972 | Harmon | 128/284 |
| 3,672,371 | 6/1972 | Roeder | 128/290 |
| 3,881,490 | 5/1975 | Whitehead et al. | 128/287 |
| 3,905,372 | 9/1975 | Denkinger | 128/285 |
| 3,929,135 | 12/1975 | Thompson | 128/287 |
| 3,959,569 | 5/1976 | Burkholder, Jr. | 428/475 |
| 4,057,061 | 11/1977 | Shikawa et al. | 128/284 |
| 4,076,663 | 2/1978 | Masuda et al. | 260/17.4 GC |
| 4,079,739 | 3/1978 | Whitehead | 128/290 R |
| 4,195,634 | 4/1980 | DiSalvo et al. | 128/290 R |
| 4,217,901 | 8/1980 | Bradstreet et al. | 128/290 R |
| 4,260,443 | 4/1981 | Lindsay et al. | 156/220 |
| 4,285,343 | 8/1981 | McNair | 128/287 |
| 4,297,410 | 10/1981 | Tsuchiya et al. | 428/283 |
| 4,324,246 | 4/1982 | Mullane et al. | 128/287 |
| 4,342,314 | 8/1982 | Radel et al. | 128/287 |
| 4,364,992 | 12/1982 | Ito et al. | 428/283 |
| 4,397,644 | 8/1983 | Matthews et al. | 604/378 |
| 4,412,833 | 11/1983 | Wiegner et al. | 604/14 |
| 4,413,986 | 11/1983 | Jacobs | 604/14 |
| 4,425,130 | 1/1984 | DesMarais | 604/389 |
| 4,463,045 | 7/1984 | Ahr et al. | 428/131 |
| 4,467,012 | 8/1984 | Pedersen et al. | 428/248 |
| 4,500,315 | 2/1985 | Pieniak et al. | 604/379 |
| 4,537,590 | 8/1985 | Pieniak et al. | 604/379 |
| 4,540,454 | 9/1985 | Pieniak et al. | 156/62.2 |
| 4,559,050 | 12/1985 | Iskra | 604/368 |
| 4,560,372 | 12/1985 | Pieniak | 604/369 |
| 4,573,988 | 3/1986 | Pieniak et al. | 604/379 |
| 4,578,068 | 3/1986 | Kramer et al. | 604/368 |
| 4,589,876 | 5/1986 | Van Tilburg | 604/385 R |
| 4,596,567 | 6/1986 | Iskra | 604/368 |
| 4,605,401 | 8/1986 | Chmelir et al. | 604/368 |
| 4,605,402 | 8/1986 | Iskra | 604/368 |
| 4,608,047 | 8/1986 | Mattingly | 604/387 |
| 4,610,678 | 9/1986 | Weisman et al. | 604/368 |
| 4,631,062 | 12/1986 | Lassen et al. | 604/385 R |
| 4,654,038 | 3/1987 | Sakurai | 604/368 |
| 4,654,039 | 3/1987 | Brandt et al. | 604/368 |
| 4,654,040 | 3/1987 | Luceri | 604/385 R |
| 4,681,578 | 7/1987 | Anderson et al. | 604/385 R |
| 4,687,478 | 8/1987 | Van Tilburg | 604/387 |
| 4,693,713 | 9/1987 | Chmelir et al. | 604/368 |
| 4,701,178 | 10/1987 | Glaug et al. | 604/387 |
| 4,755,413 | 7/1988 | Morris | 428/138 |
| 4,798,601 | 1/1989 | Shirose et al. | 604/368 |
| 4,798,603 | 1/1989 | Meyer et al. | 604/378 |
| 4,801,494 | 1/1989 | Datta et al. | 428/283 |
| 4,846,829 | 7/1989 | Lloyd | 604/389 |
| 4,892,534 | 1/1990 | Datta et al. | 604/370 |
| 4,908,026 | 3/1990 | Sukiennik et al. | 604/378 |
| 4,950,264 | 8/1990 | Osborn, III | 604/385.1 |

FOREIGN PATENT DOCUMENTS

| | | |
|---|---|---|
| 59-225058 | 12/1984 | Japan . |
| 61-179151 | 8/1986 | Japan . |
| 07536 | 5/1992 | World Int. Prop. O. . |
| 07537 | 5/1992 | World Int. Prop. O. . |

THIN SANITARY NAPKIN HAVING A CENTRAL ABSORBENT ZONE AND A METHOD OF FORMING THE NAPKIN

This is a continuation of copending application Ser. No. 07/556,694 filed on Jul. 19, 1990, now abandoned.

FIELD OF THE INVENTION

This invention relates to a thin sanitary napkin and a method of manufacturing the napkin. More specifically, this invention relates to a thin sanitary napkin which has a caliper of less than about 5 millimeters and which has a longitudinally-extending central absorbent zone which is more absorbent and stiffer than adjacent zones so as to resist twisting and bunching during use.

BACKGROUND OF THE INVENTION

Sanitary napkins, also referred to as catamenial or feminine pads, are designed to be worn by a female to absorb medium to heavy flow of body fluids such as menses, blood, urine, and other excrements discharged by the body during a menstrual period. Sanitary napkins are external devices which are designed to be aligned approximate the pudendum region of the human body and are generally held in position by being adhesively or mechanically attached to an undergarment. Such products differ from tampons which are classified as internal devices and are designed to be physically inserted into the vaginal cavity. Sanitary napkins also differ from pantiliners and panty shields in several noticeable ways. Sanitary napkins are generally larger in size, have a more defined three-dimensional configuration, are thicker in caliper and are bulkier in appearance than pantiliners or panty shields. Functionally, sanitary napkins are different in that they are constructed to absorb a greater quantity of body fluid and are designed so that they can be worn for a longer period of time; for example, overnight if needed.

Since sanitary napkins are normally used during the major discharge portion of a menstrual period, they are constructed to handle medium to heavy flows and commonly have a total absorbent capacity in the range of about 20 to 50 grams of fluid. Pantiliners and panty shields, on the other hand, are designed to absorb relatively small amounts of body fluids and are marketed to be used at the beginning and end of a menstrual period when flow is light or spotty. Commercially available pantiliners and panty shields are constructed to have a total absorbent capacity in the range of about 1 to 15 grams of fluid.

Today's sociological changes have enabled women to become more active in sports and other types of physical activity. These changes have been complemented by a change in attire and have given women the option of wearing tight, body-fitting clothing. Current sanitary napkins, having a caliper of 6.4 mm or greater, can present an unsightly bulge adjacent the pudendum when worn inside tight-fitting shorts or pants. The overall size and configuration of the napkin can also restrict leg movement or cause discomfort when a women participates in physical or sporting events. In view of this, there is a real need to develop a thin sanitary napkin which is less than about 5 millimeters in caliper yet able to absorb as much body fluid as current available products.

In developing a thin sanitary napkin less than about 5 millimeters in caliper, it was realized that such products had a tendency to twist and bunch when worn. The squeezing of the napkin between the thighs and the resulting deformation as a woman moves about, causes the upper surface of the napkin to acquire a curved or convex shape. This twisting and bunching is referred to as "roping" because a cylindrical profile can be imparted to the sanitary napkin. This roping effect is detrimental because the napkin is unable to absorb body fluid that contacts its upper surface. The fluid discharged from the vagina has a tendency to run off the roped napkin before it can be absorbed and, therefore, the fluid leaks onto the undergarment. This run-off becomes significant during periods of heavy flow.

It has been found that by positioning an absorbent strip, which is stiffer and more absorbent than adjacent portions, along the longitudinal central axis of the sanitary napkin, this roping phenomenon can be mitigated and/or eliminated.

Other manufacturers have recognized the need for a thin sanitary napkin but have not addressed the roping problem. U.S. Pat. No. 4,950,264, issued to Thomas W. Osborn, Ill., teaches a thin sanitary napkin. The Osborn application teaches a thin sanitary napkin comprised of an absorbent and a liquid-impermeable barrier. Claim 1 teaches that the sanitary napkin has a flexure-resistance of less than about 300 grams, a test capacity of at least about 8.0 grams, and a total capacity of at least about 20.0 grams. The Osborn application also teaches that the thin sanitary napkin is under 5.0 millimeters in caliper and has a capacity sufficient to absorb medium or heavy flows. However, Osborn does not teach the presence of a longitudinally-extending central absorbent zone, which is less than about 2 inches wide, and which is stiffer and more absorbent than adjacent portions of the napkin.

U.S. Pat. No. 4,079,739 issued to Howard A. Whitehead and assigned to the present assignee teaches a feminine pad having a thick central layer of absorbent material. The thick central layer does not contain superabsorbent as does the laminate taught in the present invention.

Other patents, which teach various aspects of this invention, include the following: U.S. Pat. No. 3,065,751 issued to Gobbo et al. which teaches a disposable diaper having a certain Gurley stiffness and having a flexible absorbent layer; U.S. Pat. No. Re. 32,649 issued to Brandt et al. which teaches hydrogel forming polymer compositions for use in absorbent structures and at column 18, lines 40-43, mentions the thickness of the absorbent core; and U.S. Pat. No. 4,578,068 issued to Kramer et al. which teaches an absorbent laminate structure containing superabsorbent particles.

Now, a thin sanitary napkin has been developed which has a longitudinally-extending central absorbent zone which is less than about 2 inches wide and which is stiffer and more absorbent than adjacent portions of the napkin.

SUMMARY OF THE INVENTION

Briefly, this invention relates to a thin sanitary napkin designed to be worn by a female to absorb body fluids such as menses, blood, urine, and other excrements discharged during a menstrual period. The sanitary napkin has a liquid-impermeable baffle, an absorbent retained on the baffle, and a caliper of less than about 5 millimeters. The absorbent has a longitudinally-extending central absorbent zone with a width of less than about 2 inches. The central zone is capable of absorbing at least 20 grams of body fluid which is discharged from the vaginal cavity and deposited onto the napkin. The central zone also has a greater stiffness than adjacent portions of the napkin so as to resist twisting and bunching during use. A method of manufacturing the sanitary napkin is also disclosed.

The general object of this invention is to provide a thin sanitary napkin which has a longitudinally-extending central absorbent zone with a width of less than about 2 inches. A more specific object of this invention is to provide a thin sanitary napkin which has a caliper of less than about 5 millimeters and which has a longitudinally-extending central absorbent zone which is more absorbent than adjacent zones and stiffer, so as to resist twisting and bunching during use.

Another object of this invention is to provide a method of manufacturing a thin sanitary napkin which is less noticeable when worn under tight-fitting clothing.

A further object of this invention is to provide a sanitary napkin which uses less material and therefore is more environmentally friendly.

Still another object of this invention is to provide a sanitary napkin which is lower in cost by selectively placing expensive material, such as the superabsorbent and the transfer material, within the napkin where they are most effective while minimizing the amount of material needed.

Still another object of this invention is to provide a thin sanitary napkin which has at least three lateral zones which vary in caliper, stiffness and absorbency.

Still further, an object of this invention is to provide a thin sanitary napkin which has a relatively stiff central absorbent zone which resist twisting and bunching when worn.

Other objects and advantages of the present invention will become more apparent to those skilled in the art in view of the following description and the accompanying drawings.

DETAILED DESCRIPTION OF THE PREFERRED EMBODIMENT

Figure 1:
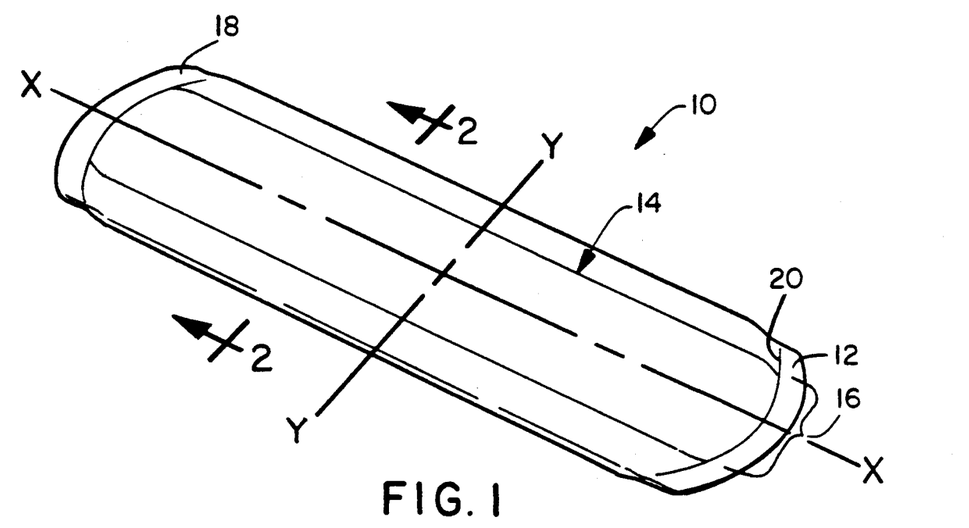
FIG. 1 is a perspective view of a sanitary napkin having a longitudinally-extending central absorbent zone.

Referring to FIG. 1, a thin sanitary napkin 10 is shown which is designed to be worn by a female to absorb body fluids such as menses, blood, urine, and other excrements discharged during a menstrual period. The sanitary napkin 10 is about 150 mm to 320 mm long, about 60 mm to 120 mm wide and has a racetrack shape with rounded ends. The napkin 10 has a caliper or thickness of less than about 5 millimeters, preferably less than about 4 millimeters, and most preferably less than about 3 millimeters. The sanitary napkin 10 includes a liquid-impermeable baffle 12 and an absorbent 14 which is secured to or retained on the baffle 12.

The liquid-impermeable baffle 12 is designed to face the inner surface, generally the crotch portion, of an undergarment (not shown). The baffle 12 permits the passage of air or vapor out of the sanitary napkin 10 while blocking the passage of body fluids and liquids. The baffle 12 can be made from a micro-embossed polymeric film such as polyethylene or polypropylene, or it can be made from bicomponent films. A preferred material is polyethylene.

The absorbent 14 can be secured to the baffle 12 by an adhesive or, alternatively, it can be enclosed by a liquid-permeable cover. The absorbent 14 has a longitudinally-extending central absorbent zone 16 aligned along the longitudinal axis, designated X—X, the napkin 10. The central absorbent zone 16 has an overall length which extends at least about 50%, and preferably about 75%, of the length of the napkin 10. More preferably, the central absorbent zone 16 extends essentially the entire length of the napkin 10 and terminates at the end seal lines 18 and 20. The central absorbent zone 16 has a width of less than about 2 inches (50.8 mm), preferably between about 0.5 and 2.0 inches (12.7 mm and 50.8 mm), and most preferably about 1.25 inches (31.8 mm). The central absorbent zone 16 can have a width which is equal to or less than the width of the absorbent 14 when measured across the central transverse axis Y—Y of the napkin 10. Preferably, the central absorbent zone 16 has a width which is less than about 60% of the width of the sanitary napkin 10 when measured across the narrowest portion of the napkin 10. The central absorbent zone 16 also has a width which is preferably less than about 75% of the width of the absorbent 14 when measured across the narrowest portion of the absorbent 14.

The central absorbent zone 16 represents the significant absorbing portion of the napkin 10 and has the capability of absorbing at least about 80%, preferably about 90%, and most preferably about 95% of the body fluid deposited onto the napkin 10. In terms of amount of body fluid, the central zone 16 can absorb at least 20 grams, preferably about 25 grams, and most preferably, about 30 or more grams of body fluid. It should be noted that the amount of body fluid which can be absorbed by the sanitary napkin 10 can be determined using a saline solution.

The capacity of the sanitary napkin 10 can be determined by the following test. In performing this test, one napkin is sufficient. The sanitary napkin to be tested is first conditioned by leaving it in a room which is at 21°±1° C. and at 50±2% relative humidity for a period of two hours. If the napkin contains a peel strip, this is removed. The entire napkin, minus any peel strip, is weighed to the nearest 0.1 gram. The napkin is then submerged in a beaker of stabilized isotonic saline which contains no preservatives. A suitable sterile saline is commercially sold by Baxter Travenol Company of Deerfield, Ill. under catalog no. B3158-2. The napkin is totally submerged and is not bent or otherwise twisted or folded. The napkin is submerged for 10 minutes. The napkin is removed from the saline and suspended for two minutes in a vertical position to allow the saline to drain out of the napkin. The napkin is then placed with the bodyside cover face down on an absorbent blotter. The blotter can be filter paper no. ED 631-25 available from the Ahlstrom Filtration Inc., Mount Holly Springs, Pa. 17065. A uniform 17.6 grams per square centimeter load is placed over the napkin to squeeze out excess fluid. The absorbent blotter is replaced every 30 seconds until the amount of fluid transferred to the absorbent blotter is less than 0.5 grams in a 30 second period. Next, the napkin is weighed to the nearest 0.1 gram and the dry weight of the napkin is subtracted. The difference in grams is the capacity of the napkin.

The central absorbent zone 16 is also stiffer than adjacent, longitudinally-extending zones. This stiffness can be obtained by making the central zone 16 thicker; by constructing it out of several layers, by using stiffer materials, by changing the basis weight or by placing another layer of material vertically adjacent to it. Preferably, the central absorbent zone has a Gurley stiffness of at least about 500 milligrams, and preferably higher. See Table 1 below.

The ability of certain zones of a sanitary napkin to resist an applied bending force, known as pad stiffness, is determined by measuring the amount of force required to bend a rectangular composite sample cut from the sanitary napkin that includes all layers excluding the peel strip. The force needed to bend each sample is measured using a Gurley Model 4171-d Digital Stiffness Tester which along with weights and precalibration strips are available through Teledyne Gurley, Troy, N.Y. The Gurley stiffness test procedure is modeled after the Technical Association of the Pulp and Paper Industry (TAPPI) method T 543 pm-84. The Gurley Digital Stiffness Tester is an instrument consisting of a balanced vane, which is center-pivoted, and to which a variety of weights can be added below its pivot point. The vane moves freely to accommodate testing in both left and right directions which would be analogous to upward and outward body flexing of the samples.

There is a two part calibration to the Gurley Stiffness Tester. The first calibration is done to ensure that the "Vane" pendulum is swinging according to specification against a known material (i.e., a brass strip). The Gurley instrument is calibrated following the Gurley Digital Stiffness Tester Instruction Manual to within 5% variation with a 50.8 mm wide by 25.4 mm long precalibrated Brass Calibration Strip, Gurley part no. 31644. The second calibration is done to ensure that the internal electronic calculations and conversions are accurate.

The samples cut from each sanitary napkin are 12.7 mm ±0.4 mm wide by 25.4 mm ±0.4 mm long. Each sample overlaps the top of the Gurley vane by 6.4 mm. During a test, the sample is moved against the top edge of the vane until the sample bends and the vane releases contact with the bottom edge of the sample. The point of release is measured by an electronic optical encoder which provides a greater degree of accuracy over the earlier model Gurley Stiffness Tester as was used in TAPPI T 543 pm-84. The electronic optical encoder also displays the result on the digital readout. The readout continuously displays readings from tests performed in both the left and right directions. The Gurley Model 4171-d also computes automatically through an internal microprocessor and displays the average of left and right bending stiffness data after each measurement. The average reading is then converted by this Gurley instrument into milligrams of Gurley stiffness relative to a sample size of 24.5 mm wide by 76.2 mm long.

The Gurley Stiffness Tester should be set up as follows. The required weight is attached and the base of the instrument is levelled by adjusting the leveling screw until the level's bubble is centered and the pendulum's pointer is indicating zero. The switches are set to correspond to the weight being used, the weight's position on the pendulum, the width of the specimen being tested, and the length of the specimen. For example: if a 25.4 mm ×12.7 mm specimen is tested with the 5 gm weight in the 25.4 mm slot, the switches would be set as follows:

| | |
|---|---|
| Weight = | 5 |
| Weight Position = | 1 inch |
| Width = | .5 inch |
| Length = | 1 inch |

The test procedure to be performed is as follows:
1. Center the specimen strip over the pendulum such that exactly 6.4 mm (0.25 inches) overlaps the top of the pendulum and exactly 6.4 mm (0.25 inches) will be held in the jaws.
2. Select an appropriate weight and a hole to give a reading between 2 and 6 on the scale. NOTE: The specimen should be brought to an approximate contact with the pendulum vane before applying force to avoid oscillation in the early stages.
3. Press the System Reset button. The display must read 00-000-00.
4. Press the Motor—Direction switch to cause the clamp arm to press the specimen against the pendulum.
5. Repeat step 4 in the opposite direction to establish both a left scale reading, a right scale reading, and an average reading.
6. Record the average scale reading.
7. Press the Select Button to attain the milligram calculation and record.
8. Repeat steps 1 through 7 for each specimen.

The following procedure should be used to obtain Gurley stiffness samples. A set of samples should be taken from five napkins. The longitudinal and transverse centerlines of each napkin is identified. The peel strip is removed and the garment adhesive is dusted with talc or corn starch. A sample 12.7 mm ×25.4 mm is cut from each napkin at the intersection of the two centerlines. Two additional samples of 12.7 mm ×25.4 mm are cut along the longitudinal centerline. The two additional samples are cut about 63.5 mm in front of and behind the first sample. The three samples from each napkin should be cut and handled carefully so as not to affect the sample stiffness. The Gurley stiffness is measured for each sample and the values are recorded as the stiffness of the central absorbent zone.

Next, one must identify parallel planes which are 63.5 mm in front of and behind the transverse centerline of the napkin. The width of the napkin is then measured at the narrowest point between the two planes so established. This is the width (C) of the napkin. The absorbent width is measured at the same point along the napkin. This is the width (B) of the absorbent. The width of the central absorbent zone is also measured at the same point along the napkin. This is the width (A) of the central absorbent zone. Points are then identified on the napkin which are located at the intersection of the parallel lines identified above and another set of lines which are parallel to the longitudinal centerline and at a distance of (C/4+6.4 mm) from the centerline. Take a 25.4 mm × 12.7 mm sample at each of these four points on the napkin. The Gurley stiffness of these samples is measured and are recorded as the stiffness of the adjacent zones.

Six additional points, three on each side of the longitudinal centerline, are identified which are about 7 mm from the longitudinal sides of the napkin. A sample 12.7 mm ×25.4 mm is cut from each of these points. The Gurley stiffness of each sample is measured and recorded as the "stiffness at the peripheral zone" of the napkin. The average for the stiffness of the peripheral zones is calculated and recorded as the "average stiffness of the peripheral zones" of the napkin. The maximum stiffness of the peripheral zones is then subtracted from the minimum stiffness of the central absorbent zone of the napkin and is recorded as the difference in stiffness between the central absorbent zone and the peripheral zones of the napkin.

The average of the values of the stiffness of the central absorbent zone is calculated and recorded as the "average stiffness of the central absorbent zone" for the napkin. The average of the values of the stiffness of the adjacent zones is calculated and recorded as the "average stiffness of the adjacent zones" for the napkin. The "average stiffness of the central absorbent zone" is then divided by the "average stiffness of the adjacent zones" and is reported as the ratio of the central absorbent zone to the adjacent zone stiffness.

The central absorbent zone 16 also has a ratio of machine direction stiffness to transverse direction stiffness of about 1.5 to 1.0, preferably about 1.8 to 1.0. Table 1 shows comparative data between the inventive product and two commercially available sanitary napkins which are relatively thin in caliper. The sanitary napkin also has a difference in stiffness between the central absorbent zone and peripheral zone of at least 150 milligrams. See Table 2 below. Lastly, the stiffness ratio of the central absorbent zone to the adjacent zones is greater than 2:1. See Table 3 below.

TABLE 1

COMPARISON OF MACHINE DIRECTION TO CROSS DIRECTION STIFFNESS Of NAPKIN OF THE CENTRAL ABSORBENT ZONE

| | No. of Samples | Machine Direction Gurley Stiffness (mg) | | |
|---|---|---|---|---|
| | | Average | Minimum | Maximum |
| Inventive Product | 15 | 695 | 561 | 905 |
| P&G Whisper Excel (with wings) | 15 | 189 | 147 | 236 |
| P&G Sheer Confidence (with wings) | 15 | 184 | 133 | 242 |

| | No. of Samples | Transverse Direction Gurley Stiffness (mg) | | |
|---|---|---|---|---|
| | | Average | Minimum | Maximum |
| Inventive Product | 15 | 392 | 278 | 560 |
| P&G Whisper Excel (with wings) | 15 | 171 | 104 | 453 |
| P&G Sheer Confidence (with wings) | 15 | 131 | 62 | 195 |

| | Ratio of Machine Direction/ Transverse Direction Gurley Stiffness Averages |
|---|---|
| Inventive Product | 1.8 |
| P&G Whisper Excel (with wings) | 1.1 |
| P&G Sheer Confidence (with wings) | 1.4 |

TABLE 2

STIFFNESS OF NAPKIN COMPARISONS OF CENTRAL ABSORBENT ZONE TO PERIPHERAL ZONES

| | No. of Samples | Central Absorbent Zone Machine Direction Test Results Gurley Stiffness (mg) | | |
|---|---|---|---|---|
| | | Average | Minimum | Maximum |
| Inventive Product | 15 | 695 | 561 | 905 |
| P&G Whisper Excel (with wings) | 15 | 189 | 147 | 236 |
| P&G Sheer Confidence (with wings) | 15 | 184 | 133 | 242 |

| | No. of Samples | Peripheral Zone Machine Direction Test Results Gurley Stiffness (mg) | | |
|---|---|---|---|---|
| | | Average | Minimum | Maximum |
| Inventive Product | 30 | 31.9 | 12.5 | 76.0 |
| P&G Whisper Excel (with wings) | 30 | 10.7 | 0.5 | 28.3 |
| P&G Sheer Confidence (with wings) | 30 | 6.2 | 0.5 | 24.7 |

| | Difference in Stiffness Central Absorent Zone (min)– Peripheral Zone (max) |
|---|---|
| Inventive Product | 485 |
| P&G Whisper Excel (with wings) | 119 |
| P&G Sheer Confidence (with wings) | 108 |

TABLE 3

STIFFNESS OF NAPKIN COMPARISONS OF CENTRAL ABSORBENT ZONE TO ADJACENT ZONES

| | No. of Samples | Central Absorbent Zone Machine Direction Test Results Gurley Stiffness (mg) | | |
|---|---|---|---|---|
| | | Average | Minimum | Maximum |
| Inventive Product | 15 | 695 | 561 | 905 |
| P&G Whisper Excel (with wings) | 15 | 214 | 133 | 278 |
| P&G Sheer Confidence (with wings) | 15 | 251 | 189 | 300 |

| | No. of Samples | Adjacent Zone Machine Direction Test Results Gurley Stiffness (mg) | | |
|---|---|---|---|---|
| | | Average | Minimum | Maximum |

TABLE 3-continued

| | | | | |
|---|---|---|---|---|
| Inventive Product | 20 | 86 | 20 | 200 |
| P&G Whisper Excel (with wings) | 20 | 167 | 136 | 220 |
| P&G Sheer Confidence (with wings) | 20 | 174 | 86 | 242 |

| | Ratio of Central Absorbent Zone/ Adjacent Zone Gurley Machine Direction Stiffness Averages |
|---|---|
| Inventive Product | 8.1 |
| P&G Whisper Excel (with wings) | 1.3 |
| P&G Sheer Confidence (with wings) | 1.4 |

Note: The machine direction referred to in Tables 1, 2 and 3 corresponds to the longitudinal direction of the napkin, i.e. axis X—X. The transverse direction referred to in Tables 1, 2 and 3 corresponds to the transverse direction of the napkin, i.e. axis Y—Y.

Figure 2:
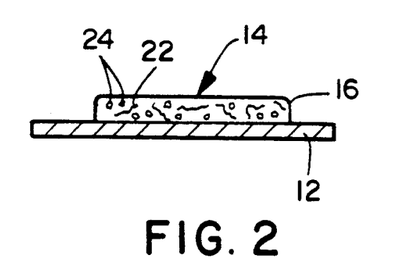
FIG. 2 is a cross-sectional view of the sanitary napkin shown in FIG. 1 taken along line 2—2.

Referring to FIG. 2, the central absorbent zone 16 is depicted as being a composite comprised of a hydrophilic material 22 and a hydrocolloidal material 24. The hydrophilic material 22 can be various natural or synthetic fibers, including cellulose fibers, surfactant-treated meltblown fibers, wood pulp fibers, regenerated cellulose or cotton fibers, or a blend of pulp and other fibers. A preferred material is an airlaid tissue. The hydrocolloidal material 24, commonly referred to as a superabsorbent, can be a hydrogel-forming polymer composition which is water-insoluble, slightly cross-linked, and partially neutralized. It can be prepared from an unsaturated polymerizable, acid group-containing monomers and cross-linked agents. Such superabsorbents are taught in U.S. Pat. Nos. 4,798,603 issued to Meyers et al., Re. 32,649 issued to Brandt et al. and 4,467,012 issued to Pedersen et al., as well as in published European Patent Application 0,339,461 to Kellenberger. These patents and the European Patent Application are incorporated by reference and made a part hereof.

Superabsorbents are very good at retaining body fluids. Superabsorbents have the ability to absorb a great amount of fluid in relation to their own weight. Typical superabsorbents used in sanitary napkins can absorb anywhere from 5 to 60 times their weight in blood. However, the absorption mechanism is not a rapid absorption and is usually slower than the rate of fluid absorption by the cellulose fluff material. The placement of the superabsorbent material in the center or lower portion of the napkin provides additional time for the superabsorbent to absorb the fluid from a transfer member.

It has been found that superabsorbents having a high mechanical stability in the swollen state, an ability to rapidly absorb fluid, and ones having a strong liquid binding capacity perform well in catamenial devices. Hydroxyfunctional polymers have been found to be good superabsorbents for this application. A hydrogel-forming polymer, specifically a partially neutralized cross-linked copolymer of polyacrylic acid and polyvinyl alcohol is preferred. After the polymer is formed, it is mixed with about a 1% anhydrous citric acid powder. The citric acid has been found to increase the ability of the superabsorbent to absorb menses and blood. This is particularly good for use in a sanitary napkin or feminine pad. The finely ground, anhydrous citric acid powder, which is void of water, along with trace amounts of fumed silica, is mixed with the polymer which has been screened to an appropriate particle size. This mixture can then be formed into a composite or a laminate structure. Such superabsorbents can be obtained from Dow Chemical, Hoechst-Celeanese, and Stockhausen, Inc., among others. This superabsorbent is a partially neutralized salt of cross-linked copolymer of polyacrylic acid and polyvinyl alcohol having an absorbency under load value above 25.

The superabsorbent 24 should have a high absorbency under load. That is, it should have the ability to expand or swell under a restraining pressure, typically about 0.3 psi. The absorbency under load value is a function of gel strength, osmotic pressure within the gel and the composition of the polymer itself. The absorbency under load value also pertains to the ability of the gel to swell against other superabsorbent particles as well as against adjacent fibers when under pressure. For purposes of this invention, a superabsorbent having a high absorbency under load is defined as having a value of 20 or higher. A preferred absorbency under load value is 25 or higher. The test for determining an absorbency under load value is taught on page 7, lines 14–52 of published European Patent Application 0,339,461 (Kellenberger) and assigned to the present assignee.

Figure 3:
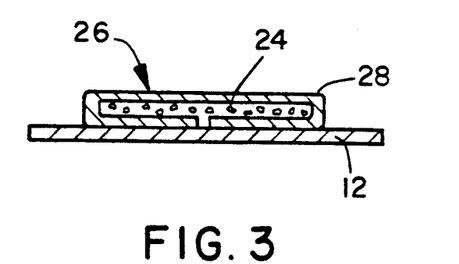
FIG. 3 is a cross-sectional view of a sanitary napkin showing an alternative embodiment wherein the absorbent is a laminate-containing superabsorbent.
Figure 4:
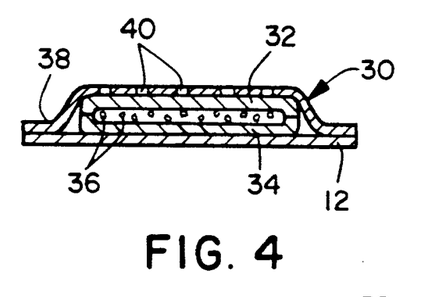
FIG. 4 is a cross-sectional view of a sanitary napkin showing another embodiment which is similar to FIG. 3 except that a cover is positioned over the absorbent.

Referring to FIGS. 3 and 4, the central absorbent zone 16 can also be constructed as a laminate 26 comprised of a hydrocolloidal material 24 positioned within a folded hydrophilic material such as a pulp layer 28. In FIG. 4, a laminate 30 is shown wherein two airlaid webs 32 and 34 enclose a superabsorbent 36 therebetween. The laminate 30 is retained in place upon the baffle 12 by a liquid-permeable cover 38. The cover 38 can be adhered about its outer periphery to the baffle 12. The cover 38 is designed to contact the body of the wearer and can be constructed of a woven or non-woven, natural or synthetic material which is easily penetrated by body fluid. Suitable materials include bonded carded webs of polyester, polypropylene, nylon, or other heat-bondable fibers. Other polyolefins such as copolymers of polypropylene and polyethylene, linear low-density polyethylene, finely-perforated film webs and net material also work well. A preferred material is a spunbonded polypropylene, non-apertured web which contains about 1 to 6% titanium dioxide pigment to give it a clean white appearance. A white uniform spunbonded material is desirable because the color exhibits good masking properties to hide menses which has passed through it and the material has sufficient strength after being perforated in the longitudinal direction to resist being torn. U.S. Pat. Nos. 4,801,494 issued to Datta et al. and 4,908 026 issued to Sukiennik et al. teach various cover materials which can be used with this sanitary napkin. These two patents are incorporated by reference and made a part hereof.

The liquid-permeable cover 38 can also contain a plurality of apertures 40 formed therein and the apertures 40 can be arranged along the longitudinal center line X—X, if desired. The apertures 40 will increase the rate at which body fluids can penetrate down into the absorbent laminate 30. The cover 38 can also be treated with a surfactant to make it more hydrophilic. The surfactant can include topical additions or internally applied materials like polysiloxanes.

Figure 5:
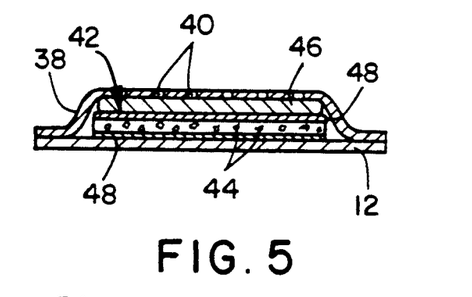
FIG. 5 is a cross-sectional view of a sanitary napkin depicting an absorbent comprised of a superabsorbent layer and a pulp layer sandwiched between a cover and a baffle.
Figure 6:
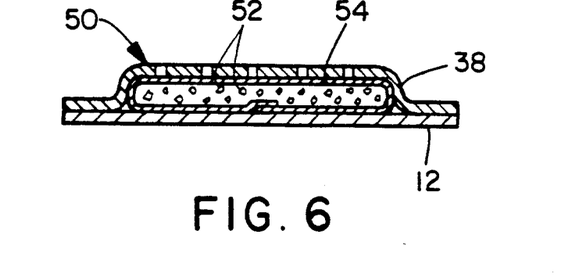
FIG. 6 is a cross-sectional view of a sanitary napkin depicting an absorbent comprised of a superabsorbent wrapped in a meltblown web and sandwiched between a cover and a baffle.

Referring to FIGS. 5 and 6, two additional laminate embodiments are shown wherein a laminate is positioned between a baffle 12 and a cover 38. In FIG. 5, a laminate 42 is shown made up of a hydrocolloidal material 44 adhered to a layer of cellulose pulp 46. The hydrocolloidal material 44 can be adhered to both the baffle 12 and the pulp layer 46 by a construction adhesive 48. It should be noted that the pulp layer 46 can also be adhered to the cover 38 and/or the baffle 12 as well. In FIG. 6, a laminate 50 is shown consisting of a hydrocolloidal material 52 completely enclosed by a nonwoven web 54. The nonwoven web 54 can be a surfactant treated meltblown web 54 which is secured to the baffle 12 and/or the cover 38 to give the sanitary napkin integrity.

Figure 7:
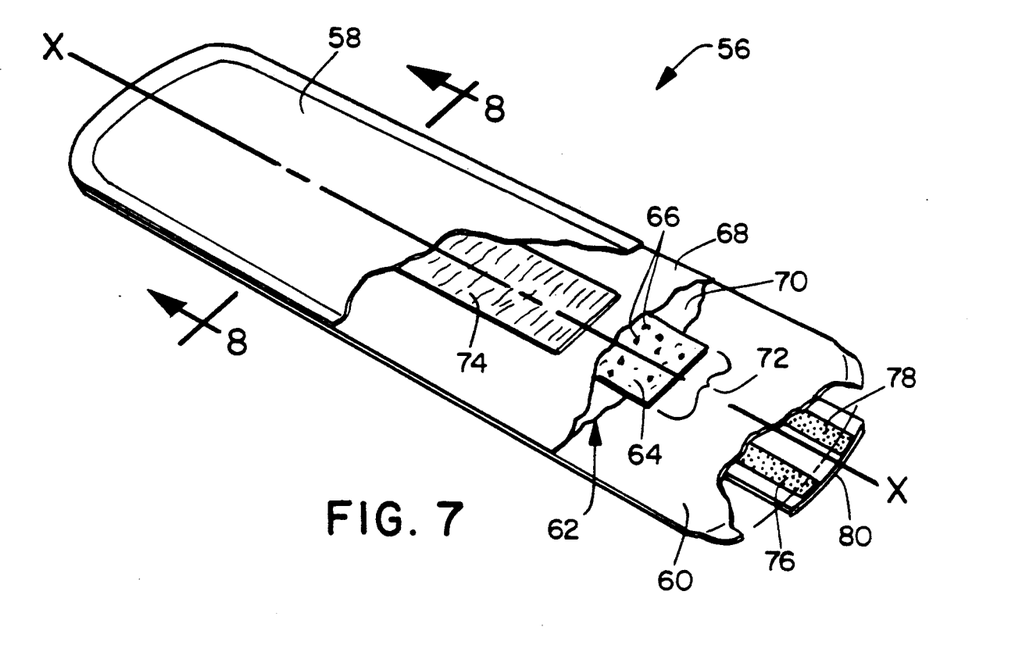
FIG. 7 is a perspective view of a sanitary napkin having a longitudinally-extending central absorbent zone enclosed between two tissue layers and aligned below a transfer layer.
Figure 8:
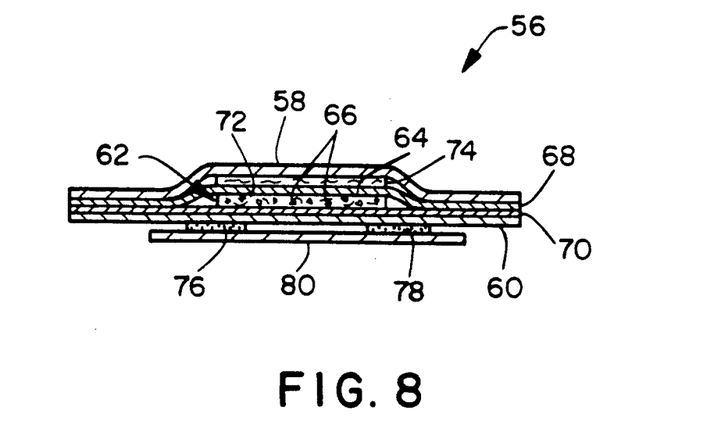
FIG. 8 is a cross-sectional of the sanitary napkin shown in FIG. 7 taken along line 8—8.

Referring to FIGS. 7 and 8, a sanitary napkin 56 is shown having a liquid-permeable cover 58, a liquid-impermeable baffle 60 and an absorbent 62 enclosed therebetween. The absorbent 62 can be a composite or a laminate which includes a hydrophilic material 64 and a superabsorbent 66. The composite or laminate is sandwiched between two layers of tissue 68 and 70. The tissue layers 68 and 70 enclose and extend laterally outward from the composite or laminate and the combination forms the absorbent 62. The absorbent 62 has a central absorbent zone 72 which is aligned along the longitudinal central axis X—X of the sanitary napkin 56. The central absorbent zone 72 is similar in construction to the central absorbent zone 16 which is shown in FIG. 1, explained above.

Positioned above the absorbent 62 is a transfer member 74. The transfer member 74 is a nonwoven polypropylene meltblown web which facilitates movement of body fluid downward and outward from the cover 58 to distant areas of the central absorbent zone 72. Preferably, the transfer member 74 is aligned along the longitudinal axis X—X of the sanitary napkin 56 and is sized and configured to correspond to the shape and dimensions of the central absorbent zone 72. A description of a transfer layer is taught in U.S. Pat. No. 4,798,603 issued to Meyer et al and assigned to the present assignee. This patent is incorporated by reference and made a part hereof.

The sanitary napkin 56 also contains two longitudinally-extending strips of garment adhesive 76 and 78 which are attached to the exterior surface of the baffle 60. The garment adhesive is commercially available from National Starch Co. located at 10 Finderne Ave. Bridgewater, N.J. 08807. The strips of garment adhesive 76 and 78 are used to secure the sanitary napkin 56 to the inside of the crotch portion of an undergarment so that it can be properly aligned with the vaginal opening. A peel strip 80 is releasably attached to the garment adhesive strips 76 and 78 and prevents the adhesive from becoming contaminated prior to attachment to the undergarment. The peel strip 80 can be a white Kraft paper coated on one side so that it can be released from a hot melt adhesive. The peel strip 80 is designed to be removed by the ultimate consumer just prior to placement of the sanitary napkin 56 in the undergarment.

Figure 9:
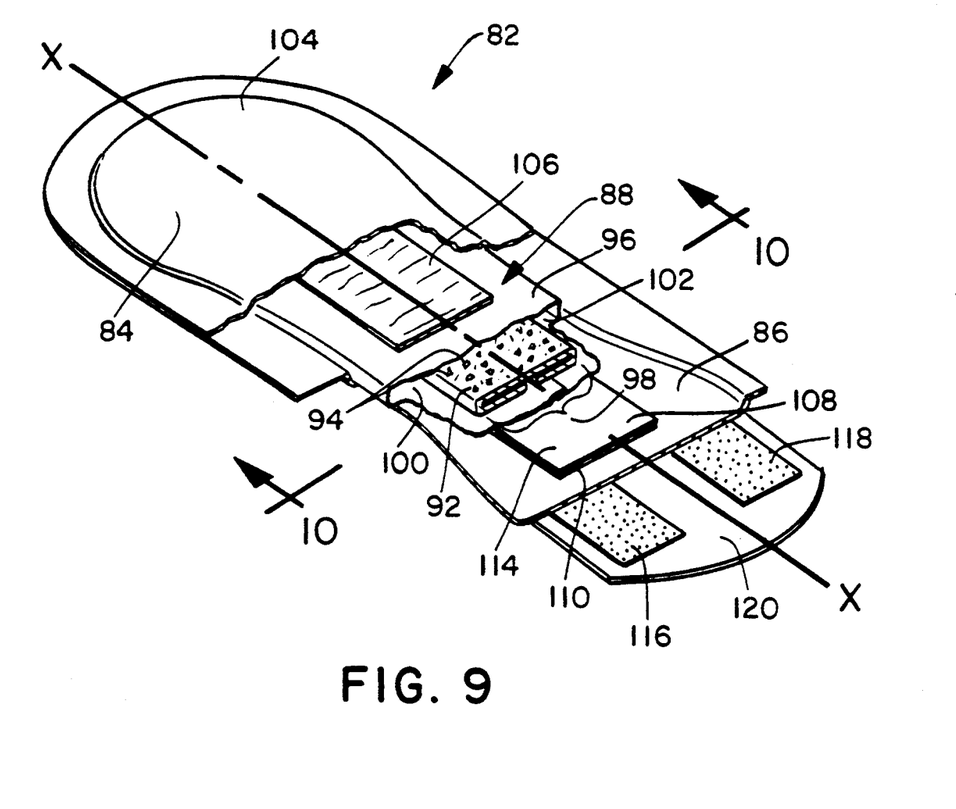
FIG. 9 is a perspective view of a sanitary napkin having a racetrack profile and having an absorbent with an hourglass profile. The absorbent extends longitudinally along essentially the entire length of the napkin and is located between a transfer layer and a wicking layer.
Figure 10:
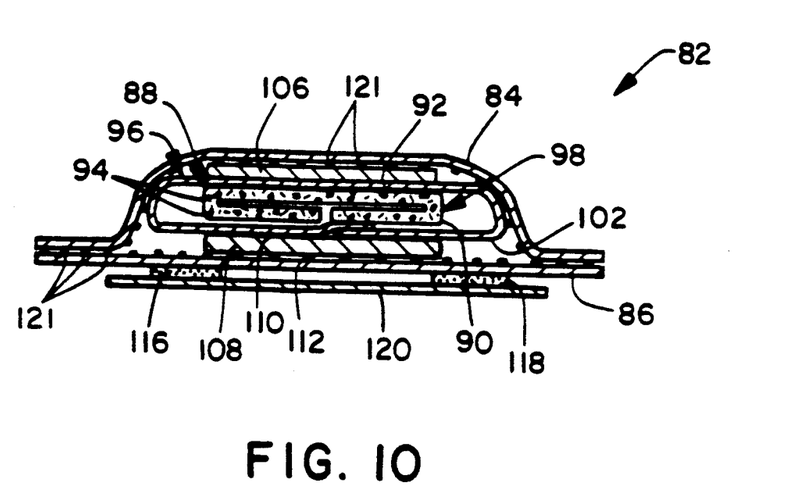
FIG. 10 is a cross-sectional view of the sanitary napkin shown in FIG. 9 taken along line 10—10.

Referring to FIGS. 9 and 10, another embodiment of a sanitary napkin 82 is shown having a racetrack profile with essentially parallel, longitudinally-extending sides which are connected by a smooth curve at each end. The sanitary napkin 82 is constructed of a liquid-permeable cover 84, a liquid-impermeable baffle 86 and an absorbent 88. The absorbent 88 is completely enclosed by both the cover 84 and the baffle 86 and is aligned along the longitudinal central axis X—X of the sanitary napkin 82. The absorbent 88 includes a laminate 90 constructed of a hydrophilic material 92 and a superabsorbent 94. Preferably, the hydrophilic material is C-folded and the superabsorbent 94 is contained therein. The absorbent 88 also includes a tissue layer 96 which is C-folded and overlapped upon itself. The tissue layer 96 extends laterally outward from the laminate 90 and is cut or formed into an hourglass profile, best seen in FIG. 9. The hourglass profile conveys a perception of comfort to the ultimate consumer.

The absorbent 88 has a central absorbent zone 98 and a pair of adjacent absorbent zones 100 and 102. The central absorbent zone 98 contains the superabsorbent 94 and represents the significant absorption portion of the sanitary napkin 82. The central absorbent zone is capable of absorbing a significant amount of body fluid, preferably at least about 20 grams, which is deposited onto the napkin 82. In FIG. 9, the central absorbent zone 98 is the area defined by the laminate 90. The adjacent zones 100 and 102 flank the central absorbent zone 98, but contain little if any superabsorbent. Preferably, the adjacent zones 100 and 102 do not contain superabsorbent. The adjacent zones 100 and 102 contain only the cover 84, the baffle 86 and the tissue layer 96. Each adjacent zone, 100 and 102, can absorb only a couple of grams of fluid but provides a lateral surface which prevents side leakage. All of the zones 98, 100 and 102 extend longitudinally at least 50% of the length of the napkin 82 and are aligned approximately parallel to the central axis X—X. Preferably, the three zones 98, 100 and 102 extend approximately the entire length of the napkin 82 and terminate at a peripheral seal line 104.

A transfer member 106 is positioned between the cover 84 and the absorbent 88 and is aligned along the longitudinal central axis of the napkin 82. The transfer member 106, as described above, can vary in size and configuration, but preferably will have a length and width which corresponds to the size of the central absorbent zone 98. The transfer member 106 is positioned vertically above the central absorbent zone 98 and facilitates movement of body fluid downward and outward from the cover 84 to distant areas of the absorbent 88.

A pulp layer 108 is positioned between the absorbent 88 and the baffle 86 and is aligned along the longitudinal central axis X—X of the napkin 82. The pulp layer 108 can be formed from a web of wood pulp fibers, such as common blotter paper and can contain a superabsorbent. The pulp layer 108 has relatively flat, first and second major surfaces, 110 and 112 respectively. One or both of the surfaces 110 and 112 can have a plurality of score lines 114 formed therein which extend parallel to the central longitudinal axis X—X of the napkin 82. The score lines 114 assist in wicking fluid lengthwise along the pulp layer 108. The pulp layer 108 preferably has a length and width corresponding to the central absorbent zone 98 and is vertically positioned below it. The pulp layer 108 facilitates movement of body fluid lengthwise to distant areas of the central absorbent zone 98. The pulp layer 108 also provides added stiffness to the central absorbent zone 98 and permits it to resist deformation when the napkin 82 is squeezed in the transverse direction. By resisting deformation, the central absorbent zone 98 is able to lay flat against the body and, therefore, will be in a much better position to absorb the body fluid discharged from the vaginal cavity.

The sanitary napkin 82 also has two strips of garment adhesive 116 and 118 secured to an exterior surface of the baffle 86. The garment adhesive provides a means for attaching the sanitary napkin to an inside surface of an undergarment. It should be noted that although two strips of garment adhesive 116 and 118 are shown, it is possible to use a single strip of adhesive or several smaller strips if desired. For best results, the sanitary napkin should have between 10 to 20 square inches of garment adhesive applied to the baffle 86. A releasable peel strip 120 is positioned over the two strips of garment adhesive 116 and 118 and serves to prevent the adhesive from becoming contaminated prior to use.

The sanitary napkin 82 also contains several locations which have been coated with a construction adhesive 121. The construction adhesive 121 serves to hold the various layers together and gives the napkin 82 integrity. Preferably, the sanitary napkin 82 will contain construction adhesive 121 to retain the cover 84 to both the baffle 86 and to the transfer member 106. The construction adhesive can also secure the pulp layer 108 to the baffle 86 and secure the laminate 90 to the tissue 96. It should be noted that the amount and location of the construction adhesive 121 can vary depending upon the size and shape of the product and the type of machine the product is manufactured on. The adhesive strength will also determine how much adhesive 121 is needed.

Figure 11:
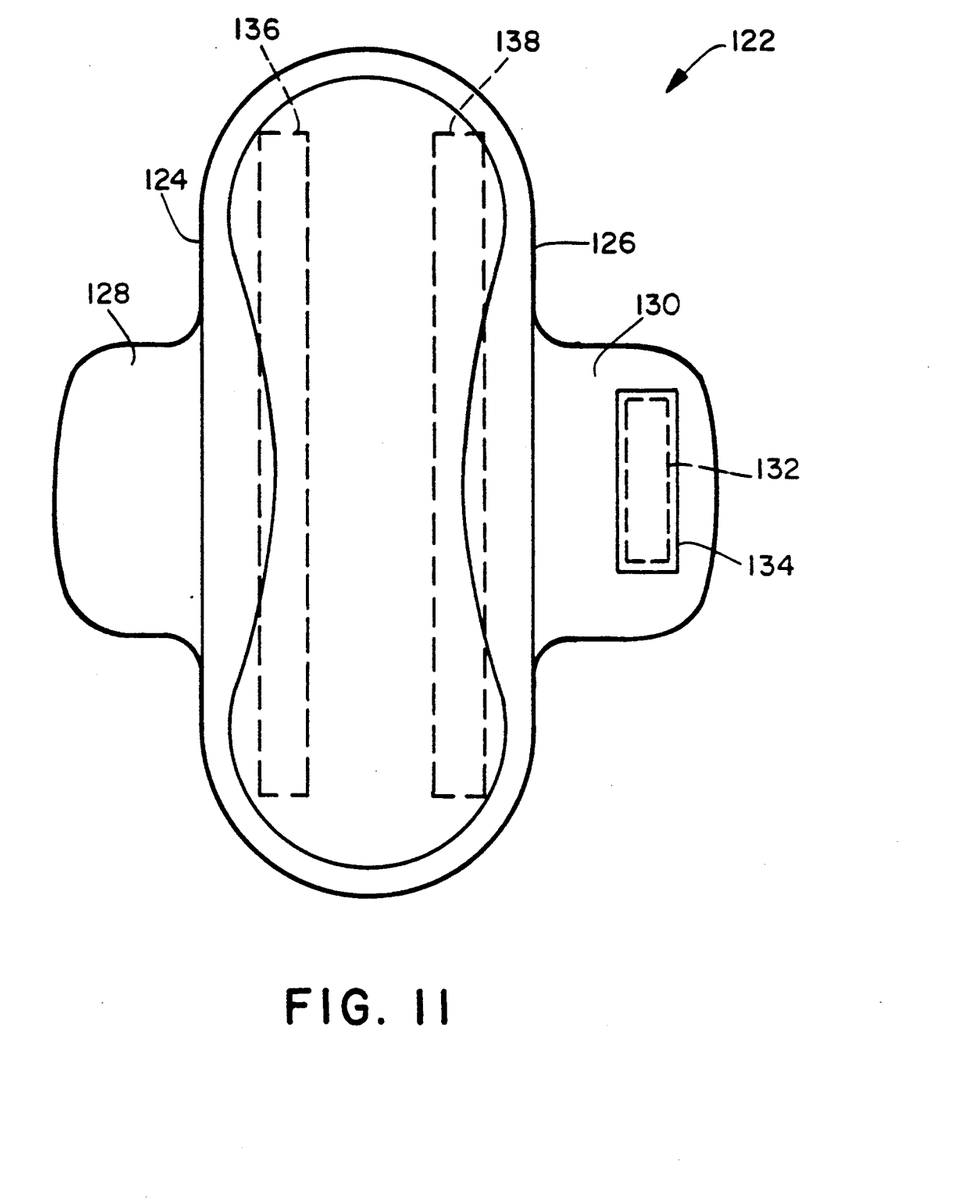
FIG. 11 is a top view of a sanitary napkin having a pair of wings attached to the longitudinal sides thereof.

Referring to FIG. 11, a sanitary napkin 122 is shown which is similar in construction to the napkin 82 depicted in FIG. 9. The napkin 122 differs in that attached to its longitudinal sides 124 and 126 are a pair of wings 128 and 130. The wings 128 and 130 extend laterally outward from the napkin 122 and are designed to wrap around the outer surface of the crotch portion of an undergarment. At least one of the wings 128 and 130 has an adhesive strip 132 attached to its upper surface which is covered by a releasable peel strip 134. The sanitary napkin 122 also has two spaced-apart garment adhesive strips 136 and 138 secured to the exterior surface of the baffle. The garment adhesive strips 136 and 138 can be covered by a releasable peel strip (not shown). When the consumer is ready to wear the product, she removes the peel strip from the bottom of the napkin 122 and adheres the napkin 122 via the garment adhesive strips 136 and 138 to the interior surface of her undergarment. She then removes the peel strip 134 and wraps the wings 128 and 130 around the exterior surface of the undergarment and adheres one wing to the other wing via the adhesive 132.

METHOD

Figure 12:
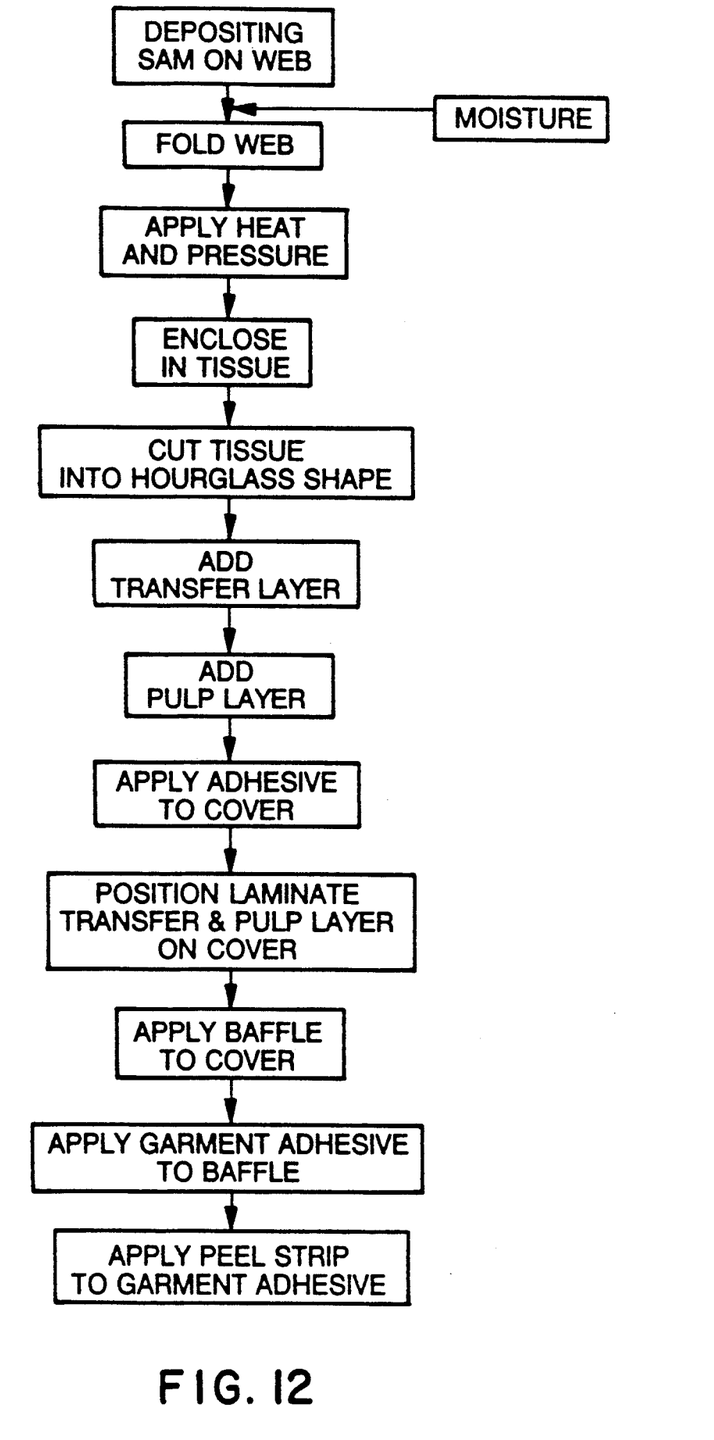
FIG. 12 is a flow diagram of a method used to manufacture the sanitary napkin of this invention.

Referring to FIG. 12, a flow diagram is depicted showing a method of manufacturing the sanitary napkin of this invention. The method includes the steps of depositing a superabsorbent onto a web of airlaid tissue. Moisture in the form of water particles or steam can be added to the airlaid tissue. The moisture causes the superabsorbent to acquire a tacky surface. Other ways to obtain a tacky surface is to treat the airlaid tissue with a hot melt pressure-sensitive adhesive, a latex binder or poly-vinyl-alcohol. The tissue is then folded about the superabsorbent to form a laminate. Conventional C-folds can be easily formed with commercially available equipment. The tacky surface on the superabsorbent aids in retaining the shape of the laminate, but it is beneficial to subject the laminate to both heat and pressure to obtain a predetermined shape. This can be accomplished by running the laminate between the nip of two rollers. The heat serves to drive off excess moisture and helps retain the fold formed in the web. The laminate is then enclosed in a tissue layer or, alternatively, it can be sandwiched between two tissue layers. The tissue layer or layers have a larger surface area than the laminate and therefore overlaps the edges of the laminate. Preferably, the tissue layer or layers are cut into an hourglass profile. The hourglass shape conveys a perception of comfort to the consumer since it is narrow at the crotch portion and allows the napkin to fit between the thighs.

The method further includes the steps of positioning the hourglass profile between a transfer member and a pulp layer to form an absorbent structure. An adhesive is applied to a major surface of a liquid-permeable cover and the absorbent structure is adhered to the adhesive. It should be noted that the absorbent structure is aligned along the central longitudinal axis of the cover. A liquid-impermeable baffle is then placed over the absorbent structure and it, too, is adhered to the cover. For best results, the baffle and the cover should have coterminous edges. Preferably, the baffle and the cover have a racetrack profile with a pair of longitudinally-extending sides. The racetrack shape conveys to the consumer a perception that the napkin has sufficient width to prevent side leakage. A garment adhesive is then applied to the exterior surface of the baffle and a releasable peel strip is positioned over the garment adhesive. The sanitary napkin is then ready to be packaged and sold.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A sanitary napkin having a longitudinal axis, comprising:
   a) a liquid-impermeable cover;
   b) a liquid-impermeable baffle;
   c) an absorbent positioned between said cover and said baffle, said absorbent having a longitudinally-extending central absorbent zone aligned along the longitudinal axis of said napkin, said central absorbent zone having a width of less than 2 inches and being capable of absorbing at least 20 grams of body fluid; and
   d) a peripheral zone aligned adjacent to said absorbent zone, said peripheral zone including said cover, said baffle and a tissue therebetween, said peripheral zone having a different stiffness than said central absorbent zone and the difference in stiffness value is greater than about 150 mg. when measured by subtracting a maximum machine direction Gurley stiffness value of said peripheral zone from a minimum machine direction Gurley stiffness value of said absorbent zone, the difference in stiffness between said absorbent zone and said peripheral zone substantially preventing bunching of said napkin when said napkin is subjected to lateral stresses, and said napkin having a caliper of less than about 5 millimeters.

2. The sanitary napkin of claim 1 wherein a sample of said central absorbent zone measuring about 2.54 centimeters by about 1.27 centimeters has a Gurley stiffness value of at least 500 milligrams.

3. The sanitary napkin of claim 1 wherein said central absorbent zone is a laminate comprised of a superabsorbent enclosed by a nonwoven web.

4. The sanitary napkin of claim 1 wherein said central absorbent zone is a laminate comprised of a superabsorbent positioned between two airlaid webs.

5. The sanitary napkin of claim 4 wherein said superabsorbent is treated with citric acid to increase its affinity to absorb menses.

6. The sanitary napkin of claim 4 wherein said superabsorbent is a copolymer of polyacrylic acid and polyvinyl alcohol.

7. The sanitary napkin of claim 4 wherein said superabsorbent is a hydroxyfunctional polymer.

8. The sanitary napkin of claim 4 wherein said superabsorbent has an absorbency under load value of at least about 20.

9. The sanitary napkin of claim 1 wherein said central absorbent zone is a composite comprised of hydrophilic fibers and a superabsorbent.

10. A sanitary napkin having a longitudinal axis, comprising:
 a) a liquid-permeable cover;
 b) a liquid-impermeable baffle;
 c) an absorbent positioned between said cover and said baffle, said absorbent having a longitudinally-extending central absorbent zone aligned along the longitudinal axis of said napkin, said central absorbent zone having a width of between about 0.5 and 2 inches and extending approximately the entire length of said napkin, said central absorbent zone capable of absorbing at least 20 grams of the body fluid, said central absorbent zone having a machine direction Gurley stiffness to transverse direction Gurley stiffness ratio of greater than 1.5:1, said stiffness ratio substantially preventing bunching of said napkin when said napkin is subjected to lateral stresses, and said napkin having a caliper of less than about 4 millimeters.

11. The sanitary napkin of claim 10 wherein said central absorbent zone is a composite comprised of meltblown fibers and a superabsorbent.

12. The sanitary napkin of claim 10 wherein said central absorbent zone is a laminate comprised of a hydrocolloid material enclosed in a hydrophilic material.

13. The sanitary napkin of claim 12 wherein said hydrophilic material is an airlaid tissue.

14. The sanitary napkin of claim 12 wherein said hydrocolloid material has an absorbency under load value of at least about 20.

15. The sanitary napkin of claim 10 wherein said absorbent is in contact with a layer of tissue which has an hourglass profile.

16. The sanitary napkin of claim 10 wherein the exterior periphery of said napkin has a racetrack profile.

17. The sanitary napkin of claim 10 wherein said central absorbent zone is comprised of a superabsorbent enclosed by an airlaid web.

18. The sanitary napkin of claim 10 wherein said central absorbent zone comprises a layer of superabsorbent adhered to a layer of cellulose pulp.

19. The sanitary napkin of claim 10 wherein said control absorbent zone is flanked by a pair of adjacent zones and said central zone is capable of absorbing about 90% of the body fluid deposited onto said napkin.

* * * * *

UNITED STATES PATENT AND TRADEMARK OFFICE
CERTIFICATE OF CORRECTION

PATENT NO. : 5,248,309

DATED : September 28, 1993

INVENTOR(S) : Paul J. Serbiak; David R. King; Patricia A. Mitchler; Alice Y. Romans-Hess; Thomas W. Van Den Bogart; Robert J. Peerenboom; Valerie V. Finch and James L. Hlaban It is certified that error appears in the above-identified patent and that said Letters Patent is hereby corrected as shown below:

Column 9, line 35, add "U.S. Patent No. before the number "4,467,012.

Column 14, line 32, delete the word "impermeable" and substitute therefor --permeable--.

Column 14, line 39, before the word "capable" delete the word "being".

Column 14, line 41, after the word "said" add the word --central-- therefor.

Column 14, line 48, after the word "said" add the word --central-- therefor.

Column 16, line 27, delete the word "control" and substitute therefor --central--.

Signed and Sealed this

Twenty-sixth Day of April, 1994

Attest:

BRUCE LEHMAN

Attesting Officer  Commissioner of Patents and Trademarks